United States Patent
Wilzbach et al.

(10) Patent No.: US 9,579,019 B2
(45) Date of Patent: Feb. 28, 2017

(54) EYE SURGERY SYSTEM AND METHOD OF OPERATING AN EYE SURGERY SYSTEM

(71) Applicant: Carl Zeiss Meditec AG, Jena (DE)

(72) Inventors: Marco Wilzbach, Stuttgart (DE); Markus Seesselberg, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 14/862,366

(22) Filed: Sep. 23, 2015

(65) Prior Publication Data

US 2016/0081549 A1 Mar. 24, 2016

(30) Foreign Application Priority Data

Sep. 23, 2014 (DE) .......................... 10 2014 014 093

(51) Int. Cl.
*A61B 3/10* (2006.01)
*A61B 3/00* (2006.01)
(Continued)

(52) U.S. Cl.
CPC .............. *A61B 3/13* (2013.01); *A61B 3/0075* (2013.01); *A61B 3/103* (2013.01); *A61B 3/107* (2013.01);
(Continued)

(58) Field of Classification Search
CPC ........... A61B 3/14; A61B 3/102; A61B 3/103; A61B 3/13
(Continued)

(56) References Cited

U.S. PATENT DOCUMENTS 8,049,873 B2 11/2011 Hauger et al.
8,333,474 B2 12/2012 Michaels et al.
(Continued)

FOREIGN PATENT DOCUMENTS

DE 10 2006 033 054 A1 1/2008
DE 10 2009 007 858 B3 7/2010
(Continued)

OTHER PUBLICATIONS

German Office Action, with translation thereof, for corresponding DE application No. 10 2014 014 093.8 dated May 19, 2015.

*Primary Examiner* — Hung Dang
(74) *Attorney, Agent, or Firm* — Patent Portfolio Builders PLLC

(57) ABSTRACT

A method of operating an eye surgery system comprises operating actuators of a stand such that an apparatus for measuring the refraction of an eye is located in a measurement position relative to the eye; measuring at least one condition of the eye and determining at least one condition value representing the at least one measured condition of the eye; measuring the refraction of the eye and determining at least one refraction value presenting the measured refraction of the eye, wherein a time distance between the measuring of the condition of the eye and the measuring of the refraction of the eye is smaller than a predetermined duration; and outputting the at least one refraction value representing the measured refraction of the eye only when the condition value representing the measured condition of the eye is within a predetermined range of values.

19 Claims, 2 Drawing Sheets

(51) Int. Cl.
    *A61B 3/13*      (2006.01)
    *A61B 3/103*    (2006.01)
    *A61B 3/107*    (2006.01)
    *A61B 3/16*      (2006.01)
    *A61F 9/007*    (2006.01)

(52) U.S. Cl.
    CPC .............. *A61B 3/1015* (2013.01); *A61B 3/16* (2013.01); *A61F 9/00745* (2013.01); *A61F 9/00736* (2013.01)

(58) Field of Classification Search
    USPC .... 351/205, 246, 206; 356/73, 497; 359/389
    See application file for complete search history.

(56) References Cited

U.S. PATENT DOCUMENTS

| | | | |
|---|---|---|---|
| 2005/0243276 A1* | 11/2005 | Van Heugten | A61F 9/007 351/205 |
| 2008/0013048 A1 | 1/2008 | Gaida et al. | |
| 2010/0214534 A1 | 8/2010 | Kuebler et al. | |
| 2011/0192405 A1 | 8/2011 | Jones et al. | |
| 2011/0202017 A1 | 8/2011 | Reimer | |
| 2015/0109580 A1 | 4/2015 | Hauger et al. | |
| 2015/0173609 A1 | 6/2015 | Seesselberg et al. | |

FOREIGN PATENT DOCUMENTS

| | | |
|---|---|---|
| DE | 20 2010 009 446 U1 | 12/2010 |
| DE | 10 2010 008 146 A1 | 8/2011 |
| DE | 10 2012 012 281 A1 | 12/2013 |
| DE | 10 2013 021 974 B3 | 3/2015 |
| EP | 2 103 249 A1 | 9/2009 |
| WO | 01/20606 A1 | 3/2001 |

\* cited by examiner

EYE SURGERY SYSTEM AND METHOD OF OPERATING AN EYE SURGERY SYSTEM

CROSS-REFERENCES TO RELATED APPLICATIONS

The present application claims priority of Patent Application No. 10 2014 014 093.8, filed Sep. 23, 2014 in Germany, the entire contents of which are incorporated by reference herein.

FIELD

The present invention relates to eye surgery systems and methods of operating eye surgery systems. In particular, the invention relates to an eye surgery system comprising an apparatus for measuring a refraction of an eye. Such eye surgery system can be used, for example, in a cataract surgery. The eye surgery system may comprise, in addition to an apparatus for measuring the refraction of the eye, a further apparatus, such as a microscope, supporting a surgeon in performing the surgery.

BACKGROUND

WO 2001/020606 A2 discloses an eye surgery system including a wave front sensor as an apparatus for measuring a refraction of an eye, and a microscope as a further apparatus supporting the surgeon. This eye surgery system can be used in a cataract surgery, wherein the surgeon may perform the surgery by observing the eye under surgery via the microscope while being able to measure a current refraction of the eye under surgery. Based on a result of the measurement of the refraction of the eye, a success of the surgery can be verified or other and additional surgery steps can be determined.

It has been found that it can be difficult for the surgeon to correctly evaluate the information and data provided by the apparatus for measuring the refraction of the eye during the surgery.

It is, accordingly, desirable to provide an eye surgery system and a method of operating an eye surgery system allowing a surgeon to evaluate and understand the information and data provided by an apparatus for measuring a refraction of an eye of the eye surgery system in a better and more reliable way.

SUMMARY

The present invention has been achieved taking the above considerations into account.

Embodiments of the present invention provide eye surgery systems and a methods of operating eye surgery systems in which an amount of information provided by an apparatus for measuring a refraction of an eye of the eye surgery system is reduced and/or presents the actual refraction of the eye with a relatively higher reliability.

The refraction of the eye describes the optical performance of the eye achieved by geometries and refractive indices of the optical components of the eye, such as a vitreous body of the eye, a crystalline lens of the eye or an intraocular lens implanted into the eye, and a cornea of the eye. The refraction of the eye may be represented by one or more parameters, such as, for example a (spherical) power, an astigmatism or a higher order visual defect.

The apparatus for measuring the refraction of the eye may comprise a wave front sensor as it is illustrated, for example, in WO 2011/020606 A2. The apparatus for measuring the refraction of the eye may, however, also include other types of sensors which do not operate according to wave front measuring principles. One example for such apparatus is a sensor as illustrated in US 2015/0109580 A1 and US 2015/0173609 A1.

According to exemplary embodiments, the apparatus for measuring the refraction of the eye is carried by a stand having plural components which are displaceable relative to each other, and plural actuators for positioning the components of the stand relative to each other. By operating one or more of the plural actuators, it is possible to adjust a position of the apparatus for measuring the refraction of the eye relative to the eye such that the apparatus is located in a measuring position relative to the eye. If the apparatus for measuring the refraction of the eye is positioned in the measuring position relative to the eye, the apparatus may determine the refraction of the eye with a high accuracy. The operation of the actuators such that the apparatus for measuring the refraction of the eye is located in a measuring position relative to the eye can be performed automatically by, for example, a controller of the eye surgery system controlling the actuators.

The control of the actuators may be performed based on a measuring signal provided by a sensor configured to directly or indirectly detect the position of the apparatus for measuring the refraction of the eye relative to the eye.

According to exemplary embodiments, the actuators are controlled based on a measuring signal provided by the apparatus for measuring the refraction of the eye itself. Based on a quality or other properties of the measuring signals generated by the apparatus for measuring the refraction of the eye, it can be possible to derive information relating to a current position of the apparatus for measuring the refraction of the eye relative to the eye.

According to further exemplary embodiments, the eye surgery system comprises a separate apparatus for measuring the position relative to the eye which is different from the apparatus for measuring the refraction of the eye. Such separate apparatus may comprise, for example, an OCT system or a camera detecting a light optical image of the eye.

According to exemplary embodiments, the eye surgery system is configured to measure at least one condition of the eye which is, in particular, related to the measurement of the refraction of the eye by the apparatus for measuring the refraction of the eye. At least one condition value representing the respective condition of the eye is determined for each of the at least one condition of the eye. A predetermined range of values can be associated with each of the at least one condition value. The eye surgery system is then further configured to output at least one refraction value representing a result of the measurement of the refraction of the eye only when the at least one condition value representing the measured condition is within the range of values associated with the respective condition value.

This is based on the assumption that the refraction of the eye can only be measured with a high accuracy if the condition of the eye allows such accurate measurement. A condition value which is within its associated range of values represents a condition which is sufficiently close to an ideal condition allowing the measurement of the refraction of the eye using the apparatus for measuring the refraction of the eye at a high accuracy. Herein, it is possible that one condition of the eye is represented by one or more condition values, and that one or more conditions are measured and monitored in order to verify that the condition of the eye sufficiently corresponds to a condition allowing the measurement of the refraction with a high accuracy.

This allows to reduce an amount of information generated by the eye surgery system as a result of the measurement of the refraction of the eye. It is, in particular, possible to output results of the measurement of the refraction of the eye only when the result represents the actual current refraction of the eye with a relatively high accuracy.

According to exemplary embodiments, the outputting of the at least refraction value is performed only when the measurements for determining the at least one refraction value and the at least one condition value are performed within a sufficiently short period of time. This may help to ensure that the current actual refraction of the eye is measured at a high accuracy and suitable for being outputted. The sufficiently short period of time can be implemented explicitly by, for example, recording measurement times for each of the measurements performed together with the condition and refraction values and selecting only those measurements condition and refraction values for further processing which are based on measurements performed within a short period of time. The short period of time can be can be a period having a duration of less than five seconds, less than two seconds or less than one second, for example. It is, however, also possible to implement the sufficiently short period of time without performing an explicit comparison of measurement times by performing the respective measurements simultaneously or in a sequence where one measurement is performed after the other. The durations of the respective measurements can be determined in advance, and the sum of these durations represents a limit of the period of time necessary to perform all of the desired measurements. If it can be determined that this limit is, for example one to ten times smaller than the short period of time mentioned above, the sequential or simultaneous performing of the measurements will be sufficient to ensure that the result of the refraction measurement represents the actual current refraction of the eye with a relatively high accuracy.

One example for the parameter representing the condition of the eye with respect to the apparatus for measuring the refraction of the eye is the position of the apparatus for measuring the refraction of the eye relative to the eye. Results of the measurement of the refraction may then be outputted only when the apparatus for measuring the refraction of the eye is located in a suitable measuring position relative to the eye.

A further example for the parameter representing the condition of the eye with respect to the apparatus for measuring the refraction of the eye is an intraocular pressure of the eye. It has been found that the intraocular pressure of the eye has an influence on the refraction of the eye. For this reason, the intraocular pressure of the eye should be from within a range of pressure values corresponding to the natural intraocular pressure of the eye when the measurement of the reflection of the eye is performed. According to exemplary embodiments, the refraction value representing the refraction of the eye is outputted only when the intraocular pressure is within a range of values from 8 mm Hg to 25 mm Hg and, in particular from within a range of values from 12 mm Hg to 18 mm Hg.

According to exemplary embodiments, the eye surgery system comprises a tonometer which can be used to determine the intraocular pressure of the eye.

According to exemplary embodiments, the eye surgery system comprises a phacoemulsification apparatus used in the cataract surgery for removing the crystalline lens of the eye, wherein the phacoemulsification apparatus comprises a pressure sensor which can be positioned within the eye or which is in fluid communication with a portion of the phacoemulsification apparatus which can be positioned within the eye.

According to further exemplary embodiments, the eye surgery system comprises a system for determining a topography of a cornea of the eye, and the measurement of the at least one condition of the eye comprises a measurement of the topography of the cornea of the eye and, in particular, a determination of the intraocular pressure based on the determined topography. It has been found that a change of the intraocular pressure of the eye results in a change of the topography of the cornea and, in particular a change of the curvature of the cornea. The intraocular pressure of the eye can be determined based on the measured topography of the cornea, accordingly.

According to exemplary embodiments herein, the topography of the eye is measured before the surgery is performed, and data representing the measured preoperative topography of the eye is stored in a memory of the eye surgery system. A surgery method may then comprise a comparison between the measured preoperative topography of the eye and the measured current actual topography of the eye measured during the surgery since a change between these two topographies allows to determine a change of the actual intraocular pressure of the eye during the surgery relative to the normal, preoperative intraocular pressure of the eye. This allows to determine the intraocular pressure of the eye for a variety of individual patients having different topographies of the corneas of their eyes.

Parameters representing the topography of the cornea may include, for example, a curvature of a surface of the cornea in a predetermined plane, two curvatures of the surface of the cornea in two different planes which intersect and which are, in particular, orthogonal relative to each other, and differences between these two curvatures.

According to exemplary embodiments, the method further comprises outputting of a signal indicating whether the condition value is within the predetermined range of values. Based on the signal, various actions can be taken. For example, the actuators of the stand can be operated based on this signal in order to move the apparatus for measuring the refraction of the eye to a measuring position relative to the eye. Moreover, the intraocular pressure of the eye can be changed based on this signal. This can be achieved by changing a pressure of a fluid supplied by a phacoemulsification apparatus. Moreover, this signal may prompt the surgeon during the surgery to check whether a speculum used to maintain the eyelids in an open position is still correctly applied.

It is possible that values representing the refraction of the eye are continuously outputted based on the results of the measurement of the refraction of the eye. However, these values are only outputted as valid refraction values when the parameter representing the condition of the eye has a condition value from within the predetermined range of values. This can be achieved by continuously displaying result data of the measurement of the refraction of the eye and by displaying a further display element only when the condition value is within the predetermined range of values. Such additional display element can be, for example, a color or some other indicator. For example, the measurement results can be displayed in green color when the condition value is within the predetermined range of values, and the values can be shown in a red color when the condition value is outside of the predetermined range of radius.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
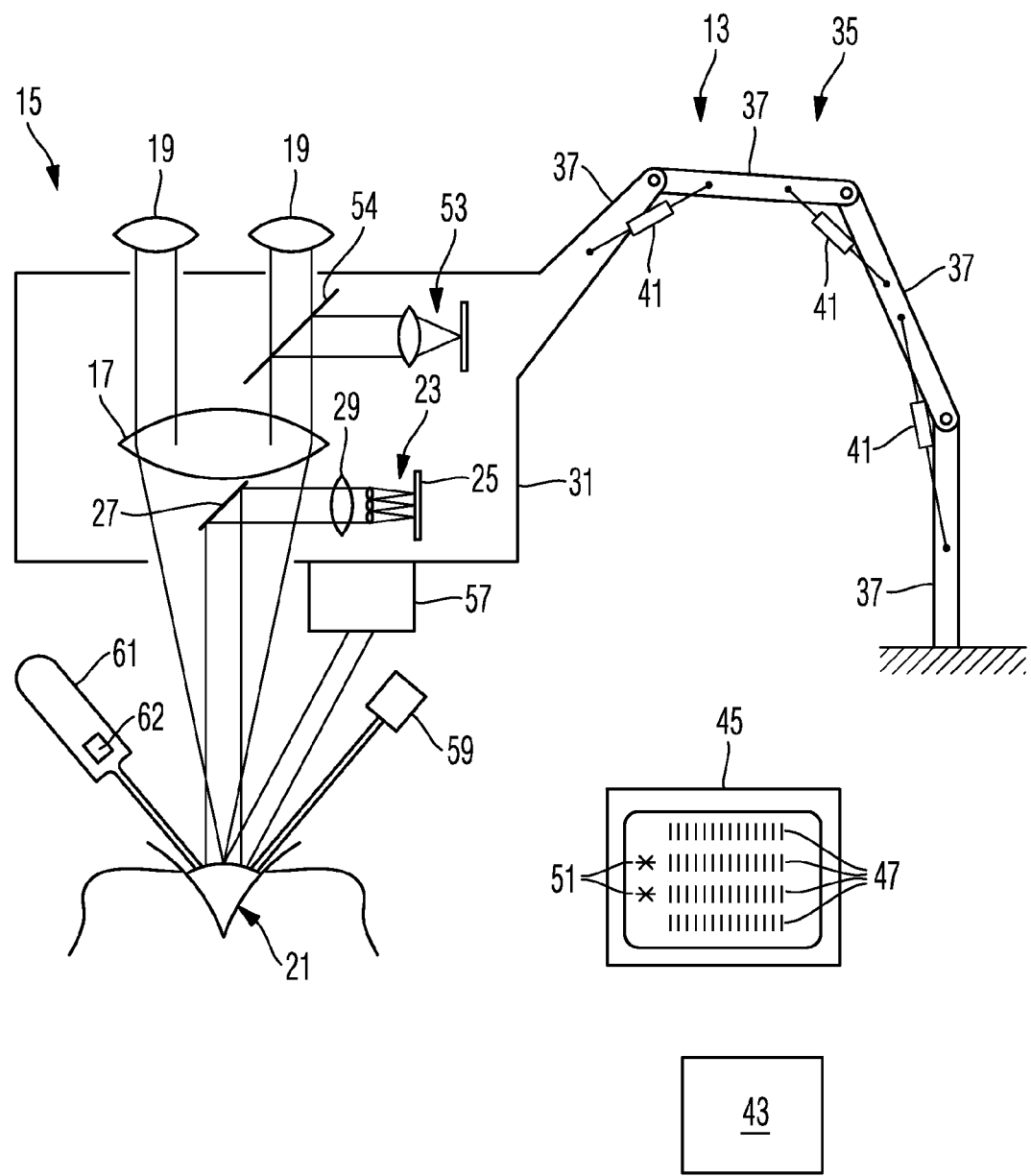
FIG. 1 is a schematic illustration of an eye surgery system.

FIG. 1 is a schematic illustration of an eye surgery system. The eye surgery system 13 is used when performing an eye surgery and comprises plural system components provided for various purposes. One system component is a microscope 15 comprising an objective lens 17 and two oculars 19. A surgeon may look through the oculars 19 in order to view a magnified light optical image of an eye 21. A further system component is an apparatus 23 for measuring a refraction of the eye 21. In the illustrated embodiment, the apparatus 23 for measuring the refraction of the eye comprises a wave front sensor 25. Wave fronts originating from the eye 21 are reflected from a mirror arranged in front of the objective lens 17 and supplied to the wave front sensor 25 via a lens 29. The wave front sensor 25 can be a Hartmann-Shack type sensor. WO 2011/020606 A2 discloses further details of such combination of a microscope 15 and an apparatus 23 for measuring a refraction of an eye.

In the present example, the microscope 15 is an exemplary system component of the eye surgery system 13 provided in addition to the apparatus 23 for measuring the refraction of the eye. As an alternative or in addition to the microscope 15, other system components can be included in the eye surgery system together with the apparatus 23 for measuring the refraction of the eye. One example for such system component is an OCT system. An example of an eye surgery system including an OCT system is illustrated in U.S. Pat. No. 8,049,873 B2. Moreover, the wave front sensor is only one exemplary embodiment of the apparatus 23 for measuring the refraction of the eye. Other embodiments of such apparatus are possible. DE 10 2012 012 281 A1 and DE 10 2013 021 974 illustrate other examples of an apparatus for measuring the refraction of the eye.

The microscope 15 and the apparatus 23 for measuring the refraction of the eye are integrated in a common housing 31, in the illustrated example. It is, however, also possible that the apparatus 23 for measuring the refraction of the eye is arranged in a housing different from a housing of the microscope 15. However, the microscope 15 and the apparatus 23 for measuring the refraction of the eye are both carried by a stand 35. The stand 35 comprises plural components 37 which are displaceable relative to each other and carries, at a distal end thereof, the microscope 15 and the apparatus 23 for measuring the refraction of the eye. The proximal end of the stand is fixed to a wall, a roof or a floor 39 of an operation room. The stand 35 further comprises plural actuators 41 in order to displace the components 37 of the stand 35 relative to each other. The actuators 41 are controlled by a controller 43 of the eye surgery system 13.

The actuators 41 are controlled by the controller 43 such that the apparatus 23 for measuring the refraction of the eye is located at a measuring position relative to the eye 21.

Also the apparatus 23 for measuring the refraction of the eye is controlled by the controller 43. For example, the controller 43 instructs the apparatus 23 for measuring the refraction of the eye to perform a new measurement, and the controller 43 receives measurement data generated by the apparatus 23 for measuring the refraction of the eye. The measurement data provided by the apparatus 23 for measuring the refraction of the eye are processed by the controller 43 in order to generate refraction values based on the measurement data, wherein the refraction values represent the measured refraction of the eye. For example, the refraction values may represent the refractive power of the eye in diopters and/or an astigmatism of the eye by a value representing an amount of the astigmatism and a value representing an orientation of the astigmatism.

The controller 43 may determine the refraction value representing the refraction of the eye based on current measurement data provided by the apparatus 23 for measuring the refraction of the eye, for example, every second, every five seconds or at other suitable time intervals. The determined refraction values can be displayed by the controller 43 on a screen 45. In the example illustrated in FIG. 1, the refraction values are displayed line by line, such that each line 47 represents one result of a measurement performed by the apparatus 23 for measuring the refraction of the eye. It is, however, also possible, that the refraction values are not displayed line by line. For example, the refraction values can be displayed always at a predetermined position on the screen 45 such that this position on the screen always indicates the currently measured refraction values such that previous refraction values, which are possibly no longer valid, are not visible.

Based on the displayed refraction values, the surgeon may verify a success of the present surgery and/or determine further necessary steps to be performed in the surgery.

As illustrated so far, this results in that the refraction values displayed on the screen 45 do often not represent the actual value of the refraction of the eye. The reason is that the conditions at which the measurements are performed by the apparatus 23 for measuring the refraction of the eye are often not the ideal measurement conditions for measuring the refraction of the eye. For example, the conditions under which the current measurements are performed deviate from suitable measurement conditions since, for example, the apparatus 23 for measuring the refraction of the eye is not sufficiently located in a measurement position relative to the eye 21 or since the current intraocular pressure of the eye 21 is outside of a suitable range or since the eye 21 of the patient is oriented in a direction relative to the apparatus 23 for measuring the refraction of the eye which is not suitable for performing the measurement. It will then be difficult for the surgeon to determine whether the displayed value is a refraction value representing the actual refraction of the eye or whether the displayed value is based on a measurement performed at improper measurement conditions.

For this reason, the eye surgery system is configured to measure at least one parameter representing a condition of the eye influencing the measurement of the refraction of the eye. A refraction value representing the refraction of the eye obtained based on a result of the measurement performed by the apparatus 23 for measuring the refraction of the eye is outputted as a valid value only when a condition value determined based on the measurement of the at least one parameter representing the condition of the eye is within a predetermined range of values. This means that the controller 43 will output refraction values obtained from the apparatus 23 for measuring the refraction of the eye only when it is determined, based on the measured condition of the eye, that the measurement conditions at which the measurement of the refraction of the eye is performed are sufficiently ideal measurement conditions.

In the example illustrated in FIG. 1, the refraction values obtained based on the measurement performed by the apparatus 23 for measuring the refraction of the eye are continuously displayed as lines 47 on the screen 45. However, not every line 47 on the screen represents a valid refraction value obtained based on a measurement at sufficiently ideal measurement conditions. Only the lines 47 indicated by an asterisk 51 or some other suitable marker or additional display element represent refraction values obtained by the apparatus 23 for measuring the refraction of the eye at times when the condition value representing the condition of the eye is within the predetermined range of values, which means that the measurement conditions for measuring the refraction of the eye are sufficiently ideal measurement conditions. If the refraction values obtained based on the measurement by the apparatus 23 for measuring the refraction of the eye are always displayed as a current value at a predetermined position on the screen 45, a valid refraction value obtained at sufficiently ideal measurement conditions can be indicated by a predetermined display feature, such as a color or an additional element, such as an asterisk.

The eye surgery system 13 comprises a camera 53 receiving light from the beam path of the microscope reflected from a semitransparent mirror 54 provided between the objective lens 17 and one of the oculars 19 such that the camera 53 detects an image of the eye similar to the image seen by the surgeon through the ocular 19. The images detected by the camera 53 are supplied to the controller 43. The controller 43 performs an image analysis of the images received from the camera 53 in order to determine whether the microscope 15 and, accordingly, the apparatus 23 for measuring the refraction of the eye are correctly positioned relative to the eye in a lateral direction (x, y). The controller 43 may determine the correct position in the lateral direction for example by determining whether the substantially circular pupil of the eye 21 is positioned at a center of the image detected by the camera 53. Based on such analysis, the controller 43 may operate the actuators 41 in order to correct the position of the apparatus 23 for measuring the refraction of the eye relative to the eye 21. The parameter representing the condition of the eye with respect to the apparatus 23 for measuring the refraction of the eye may thus represent a deviation of the center of the pupil in the image from the center of the image. For example, the distance of the center of the pupil from the center of the image may be used as a condition value. For example, the apparatus 23 for measuring the refraction of the eye may generate measurement results if this difference is within a range corresponding to −10 mm to +10 mm. However, in order to perform accurate measurements of the refraction of the eye, the apparatus 23 for measuring the refraction of the eye must be better centered relative to the eye. Therefore, it may be required that the condition value $\Delta x$ and/or the condition value $\Delta y$ is within a value range corresponding to, for example, −2 mm to +2 mm, and the controller 43 outputs valid refraction values obtained based on a measurement performed by the apparatus 23 only when the actual condition values are from within this narrower range.

Similar to the lateral position of the apparatus 23 for measuring the refraction of the eye relative to the eye, there exists a value range in the longitudinal direction (z) or distance of the apparatus 23 for measuring the refraction of the eye from the eye which must be fulfilled for performing refraction measurements at a sufficient accuracy. Therefore, a difference of the distance of the apparatus 23 for measuring the refraction of the eye from the eye and an ideal distance of the apparatus 23 from the eye can be used as a condition value. For example, a suitable predetermined range of values for this condition value may correspond to −5 mm to +5 mm. In situations where the eye is expected to have a high ametropia, the predetermined range of values can be selected narrower, such as corresponding to −1 mm to +1 mm.

The distance of the apparatus 23 for measuring the refraction of the eye can be measured, for example, by a distance sensor 57 which can be mounted on the housing 31 and which is commonly carried with the apparatus 23 for measuring the refraction of the eye on the stand 35. The distance sensor 57 can be a suitable simple distance sensor. However, the distance sensor 57 may also be provided by an OCT system (optical coherence tomography system), generating measurement data from which the distance of the apparatus 23 for measuring the refraction of the eye from the eye 21 can be derived.

The result of the measurement of the refraction of the eye is further influenced by the intraocular pressure of the eye. Therefore, also the intraocular pressure of the eye may be used as a value representing a condition of the eye. A range of values of the intraocular pressure suitable for performing refraction measurements using the apparatus 23 for measuring the refraction of the eye can be 8 mm Hg to 25 mm Hg or 12 mm Hg to 18 mm Hg, for example. The intraocular pressure of the eye 21 can be determined in various ways. For example, a tonometer 59 can be used to measure the intraocular pressure, wherein the tonometer 59 must be brought into contact with the eye 21 or, wherein the tonometer 59 may measure the intraocular pressure without contacting the eye. Moreover, the eye surgery system 13 may comprise a phacoemulsification apparatus 61 for removing the crystalline lens of the eye 21. The phacoemulsification apparatus 61 may include a pressure sensor 62 which is in fluid communication with an interior of the eye 21 when the phacoemulsification apparatus 61 is inserted into the eye 23 during operation.

Moreover, the intraocular pressure of the eye can be determined by measuring a topography of a cornea of the eye 23. The topography of the cornea of the eye can be determined, for example, using the OCT system 57 or by analyzing wave fronts emerging from the eye using the wave front sensor 25. The controller 43 collects measurement values from those components of the eye surgery system 13 allowing to obtain information on the intraocular pressure of the eye 21. Based on this information, it is determined whether the condition of the eye allows to measure the refraction of the eye at a sufficiently high accuracy. Only if this is the case, the results of the measurement of the refraction of the eye obtained by the apparatus 23 for measuring the refraction of the eye are outputted by the controller 43 as valid refraction values.

Further, an orientation of the eye 21 relative to the apparatus 23 for measuring the refraction of the eye influences a result of the refraction measurement. In order to perform the refraction measurement, the patient is typically asked to look at a suitable marker provided on the eye surgery system or projected into the eye of the patient. However, it is not ensured that the patient has oriented his or her eye towards the marker exactly at that moment where the measurement is performed. Therefore, the eye surgery system 13 may comprise an apparatus for determining an orientation of the eye. Such apparatus can be provided, for example by the OCT system 57 or the camera 53. A suitable range of values corresponding to, for example, −3 degrees to +3 degrees can be predetermined, and the controller 43 may output the measurement values obtained based on the measurement performed by the apparatus 23 for measuring the refraction of the eye as valid refraction values only when a deviation between the actual orientation of the eye and an ideal orientation of the eye is within that range.

Figure 2:
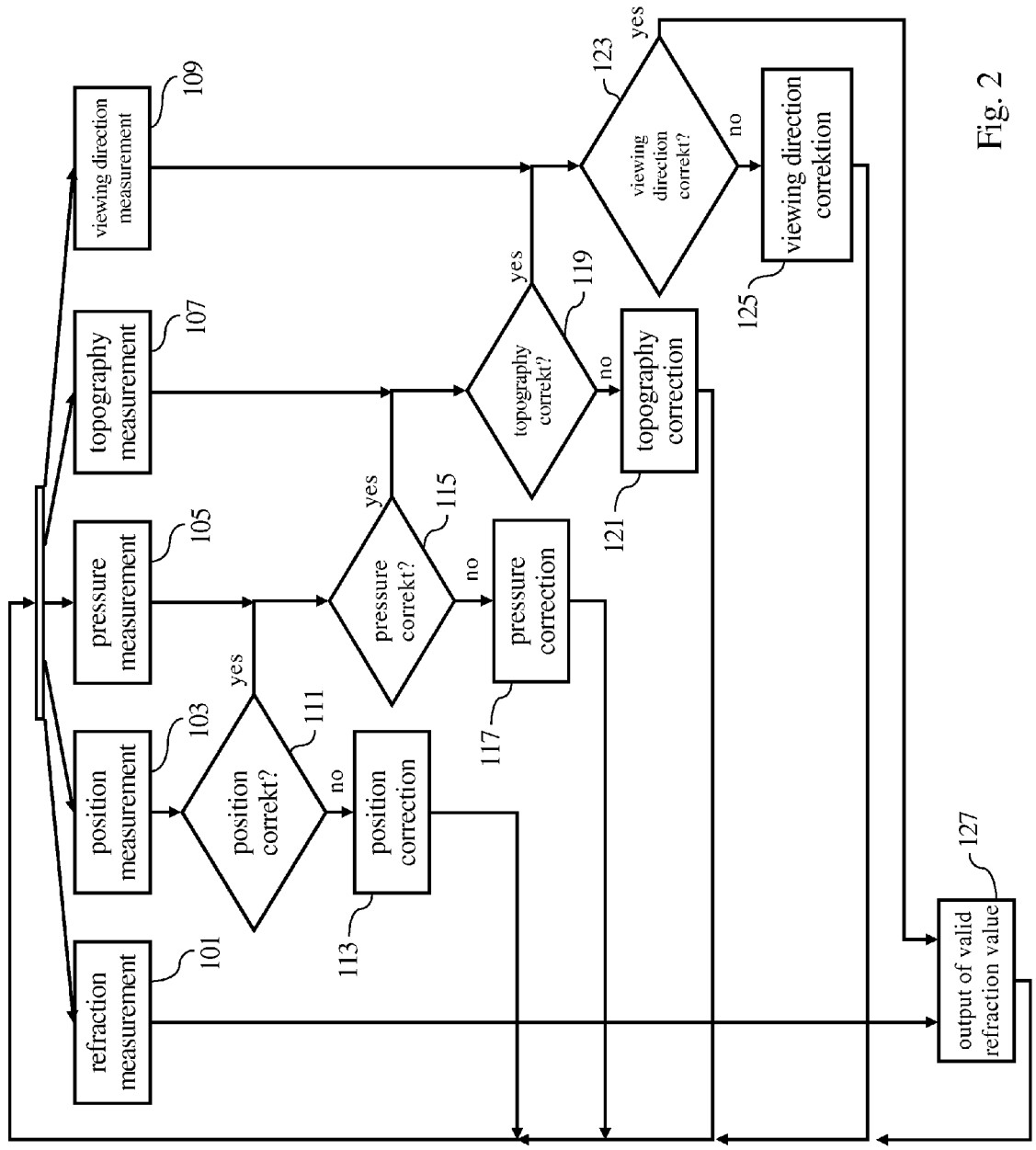
FIG. 2 is a flow chart illustrating a method of operating the eye surgery system of FIG. 1.

FIG. 2 shows a flow chart illustrating the method of operating an eye surgery system. The method comprises performing of plural measurements including a refraction measurement 101 in which at least one value is determined which represents the refraction of the eye. The method further comprises a position measurement 103 in which the position of an apparatus for measuring the refraction of the eye relative to the eye is determined. The method further comprises a pressure measurement 105 in which the intraocular pressure of the eye is directly or indirectly determined. The method further comprises a topography measurement 107 in which the shape of the cornea of the eye is determined. The method further comprises a viewing direction measurement 109 in which a direction is determined in which the eye of the patient is directed. The measurements 101, 103, 105, 107 and 109 can be performed simultaneously or sequentially. If the measurements 101, 103, 105, 107 and 109 are performed sequentially, they are performed one after the other, in any order, wherein significant pauses between two subsequent measurements are avoided. The total time necessary to perform all measurements can be, for example less than five seconds, less than two seconds or less than one second. If it is assumed that the condition of the eye does not change much within this period of time, the measurements are performed quasi-simultaneous and the measurement of the refraction of the eye is performed at substantially the same condition of the eye which are measured by the other measurements.

In a step 111 it is determined whether the position of the apparatus for measuring the refraction of the eye relative to the eye sufficiently conforms with a suitable measurement position in order to perform a sufficiently accurate refraction measurement. If this is not the case, a signal indicating the insufficient position is emitted in a step 113. Based on this signal, the controller may, for example, control actuators of a stand such that a correct measurement position is eventually achieved. If it is determined in step 111 that the position is sufficiently correct, it is determined, in a step 115, whether the intraocular pressure of the eye is within a predetermined range of values. If this is not the case, a signal indicating that the intraocular pressure of the eye does not allow a sufficiently accurate refraction measurement is emitted in a step 117. Based on this signal, the controller may, for example, control a fluid supply of a phacoemulsification apparatus in order to achieve a suitable intraocular pressure. If it is determined in step 115, that the intraocular pressure is suitable for the refraction measurement, it is determined in a step 119 whether the topography of the eye is suitable to perform a refraction measurement. For example, an incorrectly applied speculum for opening the eye lids may result in a deformation of the cornea such that a refraction measurement will indicate, for example, a false astigmatism. If it is determined in step 119 that the topography of the cornea is not suitable for a refraction measurement, a signal is emitted in a step 121, wherein the signal may, for example, request a surgeon to check the correct application of the speculum. Otherwise, it is determined, in a step 123, whether the viewing direction is correct. If this is not the case, a signal requesting correction of the viewing direction is emitted in a step 125. Otherwise, a measurement value obtained by the refraction measurement in step 101 is outputted as a valid refraction value in a step 127.

This means that valid refraction values are only outputted if the position of the apparatus for measuring the refraction is sufficiently correct, the intraocular pressure is sufficiently correct, the topography of the cornea is sufficiently correct and the viewing direction of the eye is sufficiently correct. The surgeon is not required to take notice of measurement values obtained from measurements of the refraction of the eye when the position is not correct or the intraocular pressure is not correct or the topography of the cornea is not correct or the viewing direction is not correct. It is to be noted that other suitable conditions influencing a refraction measurement can be measured and used to determine a conditions suitable for the refraction measurement.

In the example illustrated above, the refraction measurement is performed in step 101 irrespective of whether the conditions 111, 115, 119 and 123 are fulfilled or not. It is, however, also possible to perform the refraction measurement only when one or more or all of the conditions 111, 115, 119 and 123 are fulfilled. It is further possible to check the conditions 111, 115, 119 and 123 in any suitable order.

It is further possible to omit one or more of the measurements illustrated in the example of FIG. 2. It is, in particular, possible to omit the measurement of the viewing direction and/or the measurement of the topography and/or the measurement of the intraocular pressure.

The microscope 15 of the eye surgery system illustrated with reference to FIG. 1 above comprises optics having two oculars 19 allowing the surgeon to perceive a stereoscopic image of the eye 21. Moreover, the camera 53 receives light from a beam path directed to one of the two oculars 19 in order to detect an image of the eye 21. Even though this is not shown in FIG. 1, it is possible to provide two cameras, each receiving light from one of the two beam paths directed to the two oculars 19. The two cameras may then detect stereoscopic images of the eye 21 and supply the detected images to a suitable display system such that the surgeon may perceive a stereoscopic image of the eye by observing the display system. One example of such display system is a head mounted display. It is further possible to omit the oculars and to use one or two cameras for detecting images of the eye 21 which are displayed on the suitable display system.

In the example illustrated above, the image detected by the camera 53 is analyzed in order to determine whether the eye is sufficiently centered relative to the microscope and/or the apparatus for measuring the refraction of the eye. Alternatively or in addition, the pattern detected by the wave front sensor 25 (Hartmann-Shack sensor) can be used for determining whether the apparatus is sufficiently centered relative to the eye and to correct this position, if necessary.

It is further possible to determine the suitable measurement position of the apparatus 23 during the refraction of the eye relative to the eye such that the apparatus does not detect light directly reflected from the cornea of the eye since such reflected light may deteriorate the result of the refraction measurement. Such light directly reflected from the cornea is typically received by the apparatus for measuring the refraction when the measurement beam path of the apparatus for measuring the refraction of the eye coincides with the optical axis of the eye or, in other words, when the measurement beam path and the eye are exactly centered relative to each other. For avoiding such reflected light from the cornea entering the apparatus for measuring the position, it may be advantageous to use measurement positions in which the apparatus for measuring the reflection of the eye is not exactly centered relative to the eye.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. A method of operating an eye surgery system, wherein the eye surgery system comprises:
   a microscope;
   a stand carrying the microscope and comprising plural components which are displaceable relative to each other, and plural actuators for positioning the components relative to each other; and
   an apparatus for measuring a refraction of an eye which is commonly carried with the microscope on the stand; and
   wherein the method comprises:
      operating the actuators such that the apparatus for measuring the refraction of the eye is located in a measurement position relative to the eye;
      measuring at least one condition of the eye and determining at least one condition value representing the at least one measured condition of the eye;
      measuring the refraction of the eye using the apparatus for measuring the refraction of an eye and determining at least one refraction value presenting the measured refraction of the eye, wherein a time distance between the measuring of the at least one condition of the eye and the measuring of the refraction of the eye is smaller than a predetermined duration; and
      outputting the at least one refraction value representing the measured refraction of the eye only when the at least one condition value representing the at least one measured condition of the eye is within a predetermined range of values.

2. The method according to claim 1, wherein the at least one condition of the eye comprises a position of the eye relative to the apparatus for measuring the refraction of the eye; and
   wherein the at least one condition value represents the position of the eye relative to the apparatus for measuring the refraction of the eye.

3. The method according to claim 2, wherein the position of the eye relative to the apparatus for measuring the refraction of the eye comprises a distance of the eye from the apparatus for measuring the refraction of the eye; and
   wherein the at least one condition value represents the distance of the eye from the apparatus for measuring the refraction of the eye.

4. The method according to claim 2, wherein the operating of the actuators, the measuring the refraction of the eye, the measuring at least one condition of the eye and the determining of the at least one condition value are repeatedly performed until the at least one condition value is within the predetermined range of values, where-after the at least one refraction value representing the measured refraction of the eye is outputted.

5. The method according to claim 2, wherein the at least one condition of the eye comprises an intraocular pressure of the eye and wherein the at least one condition value represents the measured intraocular pressure of the eye.

6. The method according to claim 5, wherein the eye surgery system further comprises a tonometer; and
   wherein the measuring of the at least one condition of the eye comprises measuring the intraocular pressure of the eye using the tonometer.

7. The method according to claim 5, wherein the eye surgery system further comprises a phacoemulsification apparatus including a pressure sensor; and
   wherein the measuring of the at least one condition of the eye comprises measuring the intraocular pressure of the eye using the pressure sensor of the phacoemulsification apparatus.

8. The method according to claim 5, wherein the eye surgery system further comprises a system for measuring a topography of a cornea of the eye;
   wherein the measuring of the at least one condition of the eye comprises measuring the topography of the cornea of the eye using the system for determining the topography of the cornea of the eye; and
   wherein the intraocular pressure is determined based on the measured topography.

9. The method according to claim 8, wherein the determining of the intraocular pressure based on the measured topography of the eye includes a comparison of the measured topography with a previously measured preoperative topography of the eye.

10. The method according to claim 5, wherein the at least one refraction value representing the measured refraction of the eye is outputted only when the condition value representing the measured intraocular pressure of the eye represents an intraocular pressure of the eye from within range from 8 mm Hg to 25 mm Hg, or 12 mm Hg to 18 mm Hg.

11. The method according to claim 1, wherein the eye surgery system further comprises a system for measuring a topography of a cornea of the eye;
    wherein the at least one condition of the eye comprises the topography of the cornea of the eye; and
    wherein the at least one condition value represents the measured topography of the cornea of the eye.

12. The method according to claim 11, wherein the at least one condition value representing the topography of the cornea of the eye represents at least one of two curvatures of a surface of the cornea in two different intersecting planes and a difference between two curvatures of a surface of the cornea in two different intersecting planes.

13. The method according to claim 1, wherein the eye surgery system further comprises a system for determining a viewing direction of the eye;
    wherein the at least one condition of the eye comprises the viewing direction of the eye; and
    wherein the at least one condition value represents the measured viewing direction of the eye.

14. The method according to claim 1, wherein the eye surgery system further comprises an apparatus for measuring a position relative to the eye, wherein the apparatus for measuring the position relative to the eye is commonly carried with the apparatus for measuring the refraction of the eye on the stand; and
    wherein the operating of the actuators is based on an output of the apparatus for measuring the position relative to the eye.

15. The method according to claim 14, wherein the apparatus for measuring the position relative to the eye comprises at least one of an OCT system, a camera and a wave front sensor.

16. The method according to claim 1, further comprising outputting a signal indicating whether the at least condition value is within the predetermined range of values.

17. The method according to claim 1, wherein the apparatus for measuring the refraction of the eye comprises a wave front sensor.

18. An eye surgery system configured to perform the method according to claim 1.

19. An eye surgery system, comprising:
- a microscope;
- a stand carrying the microscope and comprising plural components which are displaceable relative to each other, and plural actuators for positioning the components relative to each other;
- an apparatus for measuring a refraction of an eye which is commonly carried with the microscope on the stand; and
- a controller configured:
  - to operate the actuators such that the apparatus for measuring the refraction of the eye is located in a measurement position relative to the eye;
  - to measure at least one condition of the eye and determining at least one condition value representing the at least one measured condition of the eye;
  - to measure the refraction of the eye using the apparatus for measuring the refraction of an eye and determining at least one refraction value presenting the measured refraction of the eye, wherein a time distance between the measuring of the at least one condition of the eye and the measuring of the refraction of the eye is smaller than a predetermined duration; and
  - to output the at least one refraction value representing the measured refraction of the eye only when the at least one condition value representing the at least one measured condition of the eye is within a predetermined range of values.

* * * * *